United States Patent [19]

Sharp

[11] Patent Number: 4,641,541
[45] Date of Patent: Feb. 10, 1987

[54] INTERNAL MASS SPECTROMETER INTERFACE TO A GAS CHROMATOGRAPH

[76] Inventor: Daryl Sharp, 317 Woodhaven, Chapel Hill, N.C. 27514

[21] Appl. No.: 828,178

[22] Filed: Feb. 11, 1986

[51] Int. Cl.[4] .......................................... G01N 30/72
[52] U.S. Cl. ................................ 73/864.81; 73/23.1; 250/288; 250/289
[58] Field of Search ............... 73/23.1, 864.81, 864.83, 73/864.84, 864.85, 864.87; 250/288, 289; 422/89; 250/288 A

[56] References Cited

U.S. PATENT DOCUMENTS

| | | | |
|---|---|---|---|
| 3,398,505 | 8/1968 | Llewellyn | 55/16 |
| 3,712,111 | 1/1973 | Llewellyn | 73/23.1 |
| 3,912,470 | 10/1975 | Fluckiger | 55/386 |
| 3,926,561 | 12/1975 | Lucero | 73/23.1 X |
| 3,936,374 | 2/1976 | Bradley | 210/31 C |
| 3,957,470 | 5/1976 | Dawes | 55/342 |
| 4,004,881 | 1/1977 | Ligon, Jr. | 73/23.1 |
| 4,137,750 | 2/1979 | French et al. | 250/288 X |
| 4,209,696 | 6/1980 | Fite | 250/288 X |
| 4,298,795 | 11/1981 | Takeuchi | 250/288 X |
| 4,391,778 | 7/1983 | Andresen | 250/288 X |
| 4,394,263 | 7/1983 | Dosch et al. | 55/386 X |
| 4,479,380 | 10/1984 | Novotny et al. | 73/61.1 C |
| 4,509,855 | 4/1985 | Gay | 356/316 X |

OTHER PUBLICATIONS

Novotry, Coupling of Open Tubular Columns with a Mass Spectrometer through the Jet-Type Molecular Separator, Chromatographia, 1969, vol. 2, pp. 350-353.
Henneberg and Schomberg, Investigation of the Performance of a New Separator with Variable Flow Capacity, Gas Chromatography, Institute of Petroleum Series, London, 1971, pp. 141-146.
Takeuchi, Hirata and Okumura, On-Line Coupling of a Micro Liquid Chromatograph and Mass Spectrometer through a Jet Separator, Anal. Chem. Apr. 1978, vol. 50, No. 4, pp. 659-660.
McFadden, Interfacing Chromatography and Mass Spectrometry, J. Chromatographic Sci., Jun. 1979, vol. 17, pp. 2-17.
Kuster and Wetzel, Test and Performance of a GC-MS Interface with a Fused Silica Transfer Line, Internat. J. Mass Spect. and Ion Physics, 1983, vol. 46, pp. 173-176.
Vestal and Fergusson, Thermospray Liquid Chromatograph/Mass Spectrometer Interface with Direct Electrical Heating of the Capillary, Anal. Chem. 1985, vol. 57, pp. 2376-2378.
Arrendale, Severson and Chortyk, Open Split Interface for Capillary Gas Chromatography/Mass Spectrometry, Anal. Chem. 1984, vol. 56, pp. 1533-1537.

*Primary Examiner*—Jerry W. Myracle
*Assistant Examiner*—Tom Noland
*Attorney, Agent, or Firm*—Lynn E. Barber; Paul Overhauser

[57] ABSTRACT

A device for sensitive analysis of unknown organic samples is disclosed. The device is particularly useful as an interface between a gas chromatograph and a mass spectrometer which has a high pumping capacity. The device comprises an interface internal to the mass spectrometer which may either be attached directly to an inlet probe inserted into a mass spectrometer or directly to the source body of a mass spectrometer. In both cases, the sample goes directly into the source cavity and an auxiliary vacuum system is not required for sample enrichment. For mass spectrometers with marginal pumping capacity, or when very low source pressures are required, the vacuum system may be augmented by designs which either partially or completely isolate the source and interface exhaust pumping systems from each other.

20 Claims, 16 Drawing Figures

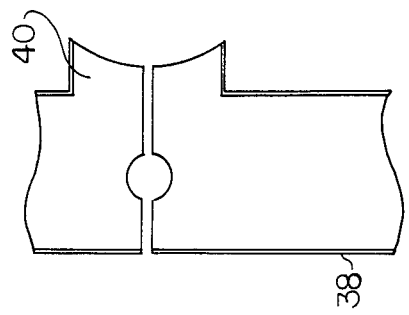
FIG 5
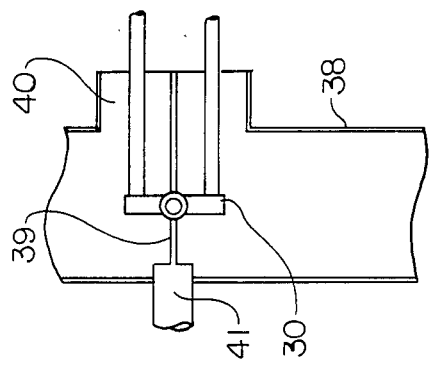
FIG 4
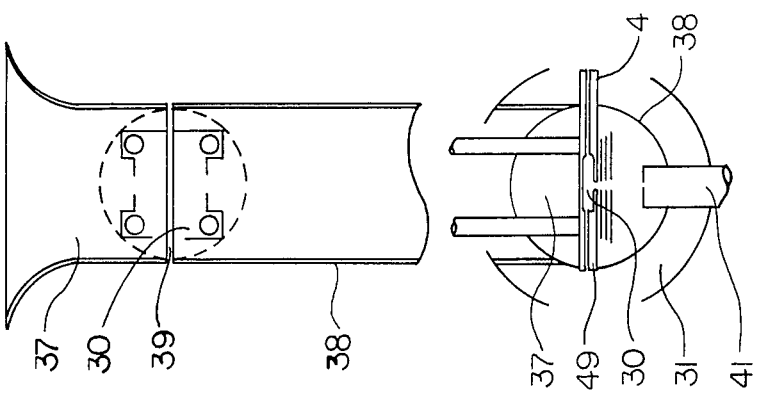
FIG 3
FIG. 6

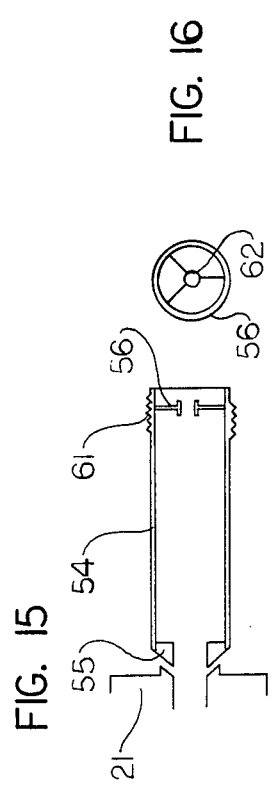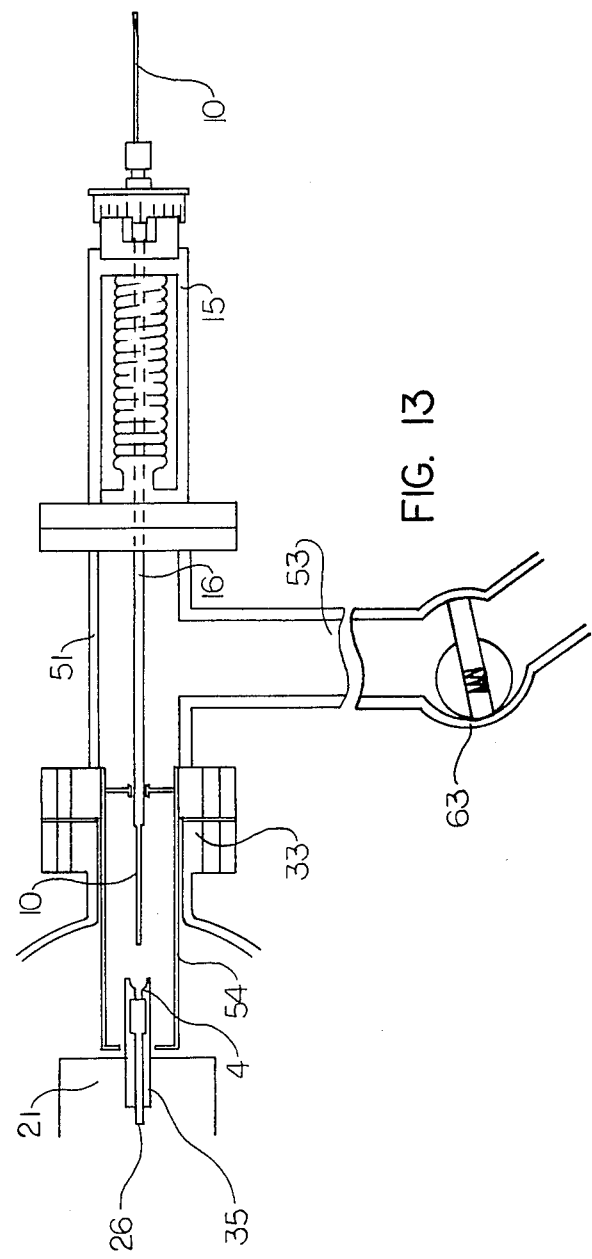

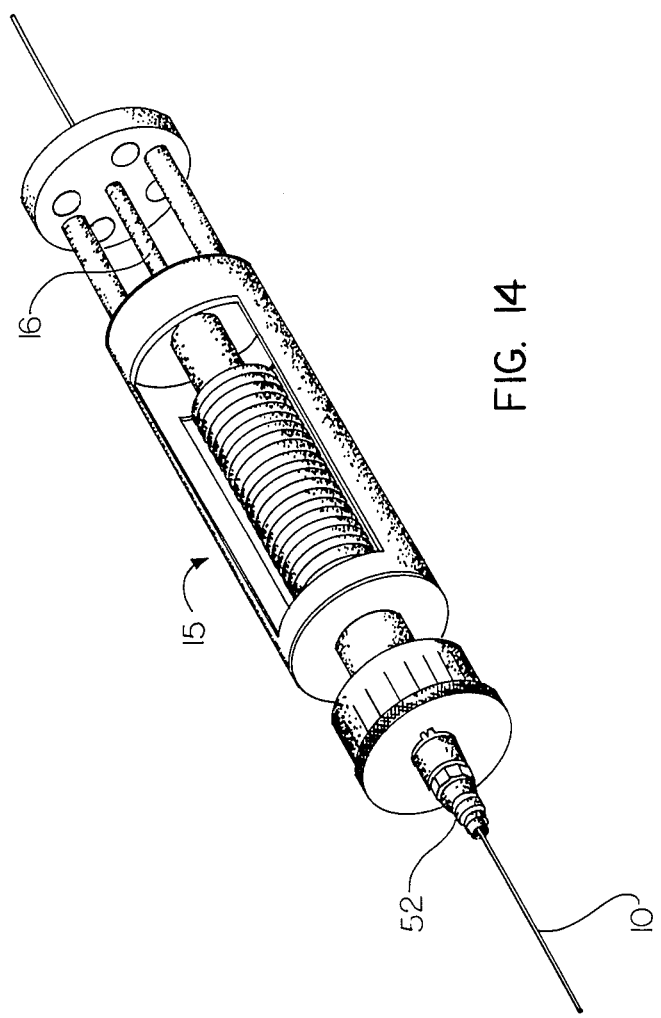

INTERNAL MASS SPECTROMETER INTERFACE TO A GAS CHROMATOGRAPH

FIELD OF INVENTION

The present invention relates to Gas Chromatography (GC) and more particularly to the combined methods and instrumentation for Gas Chromatography and Mass Spectrometry or GC/MS and pertains to an improved GC/MS source attached interface for use with mass spectrometers which have high pumping capacities.

Gas chromatography is an analytical technique of separating a mixture of organic compounds according to their volatility. This is accomplished by injecting the sample dissolved in a solvent into a carrier gas stream (usually helium) which is passed through a long capillary column having its inner walls are coated with a thin liquid film. The column is maintained at or subsequently raised to a temperature such that the sample components and solvent pass into the vapor state. The most volatile compounds are carried through the column at nearly the linear velocity of the carrier gas itself. Larger and less volatile compounds are carried through at successively lower rates. In addition, chemical interaction between the sample molecules and the liquid coating of the capillary column frequently affects sample velocity and the degree of separation of mixture components. Careful control of experimental conditions such as carrier gas flow rate, column temperature and liquid film thickness ensures that the individual compounds separate into narrow discrete bands or "peaks" as they pass through the column for maximum separation or resolution from each other. Temperature programming as opposed to isothermal analysis counteracts the natural tendency of the bands to spread with time and produces uniformly shaped peaks across the entire chromatogram or graphical display of the analysis.

When the gas chromatograph is connected to a mass spectrometer each individual compound may also be identified by its unique mass spectrum. This mass spectrum may be indicated by a graphical display of peaks representing the mass and intensity of characteristic fragments of the sample which are produced by the ionization and rupture of the sample molecule by an electron beam in the ion source of the mass spectrometer as a sample peak emerges from the GC column. Mass spectra may be obtained continuously every few seconds during the entire GC analysis. A simultaneous continuous display of a graph representing the total number of ions being produced at a given time during the analysis produces a GC chromatogram similar to that obtained by any other detection method which may be used for stand alone GC analysis. Thus, both separation and identification of individual components of a sample mixture may be accomplished in one continuous operation of combined GC/MS analysis.

This invention pertains to an alternate and much simpler method to interface a gas chromatograph with a mass spectrometer which has a high pumping capacity. The GC effluent is split between the MS ion source and the enclosing vacuum system (manifold or chamber) rather than a separate auxiliary vacuum system.

BACKGROUND INFORMATION

Up to now, the preferred standard method of interfacing a gas chromatograph to a mass spectrometer has been to insert the GC capillary directly into the MS source. Although it is inconvenient and only possible over a limited range, the MS source pressure may then be adjusted to acceptable levels for relatively high GC flows by adjusting the conductance of the source. This may be done by interchanging sources of different conductance, or by interchanging plugs or orifices in the opposite or unused sample channel of the MS source, or to a limited extent, by substituting a pump with greater speed or pumping capacity in the high vacuum system. A compromise must still be made between source pressure, analytical sensitivity and sample residence time. In general, residence time must be kept very short (less than one second) to preserve narrow capillary GC peaks. Opening the source keeps the pressure at acceptable levels and the residence time short but reduces sensitivity. The choices are much more limited with low pumping capacity mass spectrometers because of the effects of the high background manifold pressure.

With the present invention, the source pressure and the fraction of the GC effluent which flows directly to the source can be adjusted conveniently, accurately and in a continuously variable manner from zero to 100% by controlling the position of the end of the GC capillary in an interface attached to the source. In addition, considerable enrichment of the sample stream may be effected under certain experimental conditions which is not possible with a direct connection.

It should be noted that with any MS source, there must be an orifice or a short channel through which the MS capillary is inserted into the source up to some point near and perpendicular to the electron beam. It necessarily follows that there may be some slight variation in the source conductance and the flow split, depending on the exact position of the end of the column and the geometry of the channel, and on whether the opening is a channel or an orifice. This is incidental to the design and purpose of the standard source and does not compare to the present invention in which the entire inlet channel is itself an MS column which extends at all times, all the way up to the electron beam and may be calibrated very accurately for flow split.

PREVIOUSLY FILED APPLICATION

There is one related patent application by the inventor of this GC/MS source interface attachment. The pending patent application for a variable molecular separator (Ser. No. 06/748,000 filed 6/24/85) pertains to a device designed specifically to serve as an interface between a gas chromatograph and a mass spectrometer by controlling the GC carrier gas flow split between the mass spectrometer and an external auxiliary vacuum system. See FIG. 1. Sample enrichment effects which increase the ratio of sample to carrier gas can also be controlled in such a manner so as to at least partially compensate for the flow split and to maintain the quantitative sensitivity of the GC/MS analysis. Both the split and the enrichment factor can be controlled by the depth of insertion of the end of the GC column into a MS transfer column which is in effect an extension of the analytical GC column. The theory which accounts for these properties is the same for both the variable molecular separator and the present invention. By withdrawing the GC column entirely from the MS transfer column, most of the carrier gas is caused to flow to the auxiliary vacuum system and the GC flow is essentially diverted from the mass spectrometer. Incorporation of an isolation valve into the interface allows the GC column to be removed and a new column inserted without disturbing the high vacuum of the mass spectrometer. Thus, the interface also functions as a vacuum lock for the introduction of capillary columns for a variety of analytical purposes, including those of the present invention.

SUMMARY OF THE INVENTION

General

The internal GC/MS interface is a means of providing an adjustable split of a GC carrier gas between an MS source and the surrounding manifold in a mass spectrometer. The invention also allows the enrichment factor of an analytical sample to be controlled. This is accomplished by causing a GC capillary to become exactly aligned with an MS source orifice, across a narrow space exposed to the vacuum in a mass spectrometer. This space or "interface gap" provides the required flow conductance so that the carrier gas is diverted from the MS source by the MS vacuum in the interface gap. The extent of the carrier gas diversion depends on the depth of insertion of the GC capillary into the MS capillary.

Embodiments

Two embodiments of the invention will be described each of which is shown in FIG. 2. In one embodiment, the interface is attached directly to the MS source with the GC capillary becoming aligned as it is inserted. This version requires a separate column positioning device or micro-vacuum lock. The external GC/MS interface of the previous invention (variable molecular separator) serves this purpose very well. A micrometer drive/bellows mechanism developed for use with the previous invention may also be used by itself for control of the column position.

In the second embodiment of the invention, the interface is attached to a direct probe. When the interface-probe combination is inserted through a standard vacuum lock, the end of the MS transfer capillary and the end of the interface itself become aligned with the source. The MS transfer capillary is guided through a source inlet channel with the tip extending up to the center of the source. The end of the interface makes a seal with the orifice of the guide channel. In this case, either the end of the interface or the interface itself should be constructed of a material that has both sealing and electrical insulating properties.

Construction

For both embodiments, it may be convenient and useful to fabricate the interface from a single piece of stainless steel bar stock or other material. This is a relatively simple method of construction, providing increased alignment accuracy and low cost. Several interchangeable interfaces whose capillaries have different or nonuniform cross-sectional dimensions may then be used for different transmission characteristics. The fused silica or nickel MS transfer capillary may be permanently attached to the stainless steel interface using a commercially available liquid pre-polymer resin which is curable at gas chromatograph oven temperatures. This polymer is similar to the protective polyimide coating used on fused silica capillaries and to the Vespel and Vespel composites used as ferrules and valve stems in this and the other inventions. Each of the five or six commercially available Vespel composites may be used in many applications throughout the GC/MS system to take full advantage of the enhanced properties imparted by the different additives and permit the replacement of metal, ceramic or other elastomer parts. An uncoated nickel capillary may also be silver soldered to the steel interface before coating with a bonded liquid phase. In some cases, it will be advantageous to use an intermediate heavy-walled stainless steel capillary inside the bar stock to avoid drilling very narrow bores over long distances.

Use with High Pumping Capacity Mass Spectrometers

This invention has several advantages for MS systems with high pumping capacities. These MS systems often do not have sufficient GC flow capacity when they are adjusted for maximum analytical sensitivity. The advantage resulting from the addition of the internal interface of the invention is that an increase in the GC flow capacity is allowed with a minimum decrease in analytical sensitivity. High speed manifold pumping is in an attempt to relieve the problem of excess pressure in the source when the GC flow rate is high. However, source conductance is the limiting factor in determining source pressure rather than the pressure in the enclosing manifold. Increasing source conductance by enlarging source apertures reduces the source pressure but also produces a corresponding reduction in analytical sensitivity and is not a convenient way to approach the problem. High speed pumping is required for high GC flow rates even when a large percentage of carrier gas is split away from the source as with this invention because the manifold pressure must remain relatively low so that it does not begin to affect source pressure by reducing the rate of flow through source openings. Also, the residence time for sample molecules in the manifold must remain short as well in order to prevent the detection of sample molecules originating in the manifold from contributing to GC peak broadening and background contamination in the source. However, even with spectrometers with limited pump speed, some useful increase in GC flow capacity should be realized using the internal interface, depending on the relative values of the manifold conductance ($C_m$), pump speed ($S_p$) and source conductance ($C_s$) which is given approximately by the following inequality: $C_m > S_p >> C_s$, where $C_s$ is typically one liter per second and $S_p$ varies from 50 to 500 liters per second.

Use with Dual Mass Spectrometer Manifolds

The problem with use of direct GC/MS connections is that no advantage can be accomplished by separate or differential pumping of the MS source and manifold and there is no possibility for molecular enrichment of the sample beyond that which always occurs in low pressure sources. In this invention, the effectiveness of the interface can be enhanced further by the addition of a thin cylindrical stainless steel shell dividing the manifold into central and annular sections enclosing the source and extending down to the single high vacuum pump. See FIGS. 3-6. By this means the source and separator exhaust systems can be isolated from each other with negligible cross-conductance except at the pump. The effectiveness of this method will depend on the magnitude of the original $C_m/S_p$ ratio and the magnitude of enrichment effects in the interface. Pure differential pumping of the separate souce and interface effluents can also be achieved by this means with the addition of a second high vacuum pump connected through a separate port in the outer manifold. In this case, the internal separator could be just as effective as the external interface of the previous invention. In this case, the internal interface can be even more effective than the external interface of the previous invention as a result of the very low pressures possible in the interface gap.

Another convenient and potentially effective arrangement of the invention to enhance sample enrichment is to use the external and internal interfaces as the first and second stages of a two-stage molecular enrichment separator.

Control of Flow Split

An advantage of both embodiments of this invention is that their use allows splitting of the flow of the sample depending on the position of the inner capillary (column exit position or CEP) relative to the MS source orifice. Thus, the flow split is not dependent on the pressure in the MS source or vacuum system as long as this is small compared to the pressure within the interface. This condition may be easily satisfied for typical GC flow rates. For this reason, an external separator exhaust system of relatively low capacity may be connected to the interface through the same MS port to be used for more effective operation of the internal interface. (FIGS. 13 and 15) However, with large diameter connections and high speed external pumping, a high vacuum interface gap is also possible with this arrangement.

Control of Percent Transmission

Much more precise control of the column exit position (CEP) of the end of the GC capillary is required in order to accurately control the carrier percent transmission (CPT) for the short MS transfer capillary of this invention than for the long MS capillary of the previous invention (see FIG. 7 of the pending application, above). However, it also follows that only very short adjustments in the CEP are required in order to make significant changes in the CPT to the MS source. With an adjustment of less than 1 cm in the CEP, the CPT can be varied from zero to between sixty and ninety percent depending on the outside diameter (O.D.) of the GC capillary, using a MS capillary with a 0.053 cm inner diameter (I.D.) The optimum position will be determined by the source conductance and pumping capacity of the particular mass spectrometer as discussed above and by the most frequently used GC flow rates.

Electronic Control of the CEP

Accurate movement of the end of the GC column in the interface is used to provide accurate carrier gas split control. A bellows attachment used for accurate closed system control of the CEP may be readily adapted to remote electronic control. For interfaces with short MS transfer capillaries where increased accuracy is required, a more refined compact version of this device can be built with a similar displacement range and resolution (1.5 cm±0.05 mm).

Another advantage of the invention is that the interface can also function as a pulse valve with rapid on/off control which has special applications for Fourier Transform Mass. Spectrometry (FT/MS). Pulse valve capability need only be a specialized function of a general purpose electronically controlled interface in which the on/off or low/high divert time cycle can be shortened to match the very rapid ionization time cycle of the FT/MS source. However, the millisecond response time will require a device with an oscillating linear drive solenoid rather than a rotary drive. Several modes of operation are possible depending on the geometry of the MS transfer capillary. Molecular enrichment effects during the low flow cycle will greatly increase the effectiveness of this type of interface.

One special adaptation of the interface may be particularly effective as a stop-flow pulse valve. In this variation, essentially none of the flow is diverted and as a result, there is no decrease in analytical sensitivity at all in the FT/MS. An MS transfer capillary with an ID that is as small as practical is used so that there is very little annular space between it and the inserted GC capillary. As a result, the GC flow away from the source is very low at any CEP. Rapid low/high oscillations of the CEP produce corresponding pressure oscillations in the MS source. It is apparent from geometry considerations that there will be negligible back flow into the MS capillary from the source during the withdrawal or stop flow cycle and that the orifice with its large contribution to the impedance of the short MS capillary will act as a time-lag gate or valve against forward flow into the MS during the withdrawal cycle. Nearly square wave source pressure oscillations will be produced for a short MS transfer capillary. Longer MS transfer capillaries will produce damped and rounded oscillations which may nevertheless be effectively synchronized with the ionization and "ion storage" cycle of the FT/MS.

In order to function as an effective pulse valve, a first requirement is that the interface should have a MS transfer capillary that is as short as possible in order to achieve the rapid cycle times and steep CPT curve required and to minimize mechanical friction and wear in the capillaries involved. In a particular MS system additional experimentation will allow determination of best pulse frequency and magnitude of CEP change to achieve the MS source pressures desired. For a pulse valve, CEP changes involving complete withdrawal of the GC capillary from the MS capillary will require extreme alignment precision for these capillaries and should be avoided if possible.

The interface may be used to duplicate all of the functions of a currently-used metal valve over a wider and more flexible flow range, while avoiding most of its limitations. Currently-used FT/MS pulse valves are conventional low dead volume metal valves, adapted to high frequency solenoid control, which function as on/off divert valves between the MS and an auxiliary vacuum. These high-frequency valves have a severe temperature limitation as well as the problem of sample exposure to active metal surfaces. Also, the flow restriction in each branch of the "T" of the valve must be carefully matched to avoid disturbance of the GC flow rate and GC peak shape. Sample residence time in a long narrow capillary can also be a factor which affects GC peak widths. These problems can be more easily avoided with vacuum exhaust GC and a short internal interface. High pressure or restricted exhaust GC also prevents the use of the stop-flow technique discussed above.

Normally, the vacuum flange connections of an external interface to the MS make it difficult to reduce the length of the MS capillary to much below 20 cm. A very short MS capillary is possible, however, with an internal interface when the interface essentially becomes a part of the MS source as in this invention. A direct attachment of a short interface to the MS source is most useful when the overall pumping capacity of the MS itself is very high since the GC flow is split between the MS source and the enclosed MS chamber instead of to an auxiliary vacuum system. For a 3 cm MS transfer capillary only a short stroke of approximately one cm is required to cover the split range from zero (less than 0.1 percent) to 80 percent depending on the cross-sectional dimensions of the capillaries involved.

Advantage of a Short Interface

Another advantage of this invention is that because it comprises an interface having a shorter MS transfer capillary than other interfaces, the sample residence time in the interface, which is related to the length (L) and radius (a) of MS capillary by ($L^2/a$), is reduced below the level at which it would affect GC peak width. For this reason, except for very large or polar compounds, GC separation efficiency is not affected by whether or not the MS transfer capillary is coated with a chromatographic liquid film.

Higher Enrichment

The potential also exists in this invention for high molecular enrichment effects in spite of the reduced interface pressure expected from a much shorter, higher conductance interface. Nonmolecular flow conditions are a requirement for molecular enrichment effects. One approach to the problem is to design a separate interface primarily for molecular enrichment of the sample which may be only marginally useful for adjustment of the percent transmission of the carrier gas. This may be accomplished by the use of capillaries with nonuniform cross sections.

Tapered MS capillary

The decreased flow impedance of a shortened MS capillary may be readily compensated for by decreasing the I.D. of the capillary because of the dependance of the impedance on the length and radius ($1/a^3$). Since it is best to use GC capillaries of at least 0.025 cm I.D. for reasonable analytical sensitivity, increasing the interface pressure to nonmolecular flow levels by this means is limited also. However, the use of a tapered MS transfer capillary offers an ideal solution to the problem. The impedance of the MS transfer capillary may be increased by decreasing the I.D. of the MS transfer capillary at its mass spectrometer end while maintaining an optimum orifice I.D. for easy insertion of the GC capillary and maximum molecular enrichment effects. Changing the taper of the MS capillary should provide the means of controlling the enrichment factor (E) and the percent transmission (CPT) of the carrier gas much more independently of each other than is possible with a nontapered MS transfer capillary. Increasing the taper further to an extent that the cross-sectional area of the MS orifice of the transfer capillary is less than that of the internal area of the GC capillary will induce supersonic flow in either the GC or MS orifices of the capillary depending on the CEP. This supersonic flow may also be used to produce useful molecular enrichment effects. The carrier gas transmission curve (CPT v. CEP) for a uniformly tapered MS transfer capillary is much more complicated than for a straight capillary but it is just as accurate and useful in producing a calibration curve which can be easily verified experimentally. The GC guide channel of the internal interface may also be tapered to restrict GC flow and the interface gap may be reduced to 0.1 mm or less to readily convert the interface to an internal supersonic jet separator.

Interface Gap Modification

The interface gap of an internal interface may be much narrower than the gap for an external interface because of the much lower operating pressures in a high vacuum MS manifold. This means that much better alignment of the GC capillary passing through the gap into the MS capillary is possible for an internal or high vacuum interface. This also means that the exhaust pressure is always much lower than the pressure within the shorter MS transfer capillary in spite its increased conductance. This fact insures the accuracy and reproducibility of a calibration curve for a short interface and the effectiveness of the divert cycle of the interface when the GC capillary is withdrawn completely from the MS transfer capillary.

OBJECTS OF THE INVENTION

One object of the invention is to provide an internal GC/MS interface whereby the GC flow capacity of mass spectrometers which have relatively high-speed pumps may be conveniently increased with a minimum decrease in analytical sensitivity.

Another object of the invention is to provide a means of sample enrichment of the GC carrier gas stream passing through the interface into the MS.

Another object of the invention is to provide a GC/MS interface which may have a much shorter MS transfer capillary than is possible with external interfaces because of the length of standard vacuum flange connections.

Another object of the invention is to provide the means by which the MS source itself can function as an accurate continuously variable splitter so that both the GC flow rate and the MS source pressure may be maintained at their optimum levels during a combined GC/MS analysis.

Another objective of the invention is to provide a GC/MS interface which may be conveniently converted to a high frequency pulse valve for Fourier Transform Mass Spectroscopy (FT/MS) which avoids the limitations of currently used pulse valves.

Another object of the invention is to eliminate the problem of sample hold-up via condensation or chemical interaction between the sample and the surface of an interface between a gas chromatograph and a mass spectometer.

Another object of the invention is to provide a means by which the percent composition of trace constituents in a natural or synthetic gas mixture may be quantitatively increased to more measurable levels.

Another object of the invention is to provide a design for a versatile interface, which can accommodate condensable carrier vapors and much larger more condensable sample molecules, and can thus provide a means for interfacing a high pressure liquid chromatograph or super critical fluid chromatograph to a mass spectrometer for continuous analytical operation, depending on the nature of the active chromatographic surface of the MS transfer capillary and the pressure and nature of the flow within the capillary.

Another object of the invention is to provide the means along with MS analysis, by which the actual flow path or trajectory followed by sample molecules emerging from a column into a vacuum chamber under subsonic flow conditions may be determined and controlled.

Another object of the invention is to provide an internal GC/MS interface which permits true differential pumping of the MS source and diverted GC effluents by completely isolating central and annular exhaust manifolds with separate high vacuum pumps for each in order to increase the flow capacity from the gas chromatograph of the mass spectrometer.

Another object of the invention is to provide the means by which the internal GC/MS interface and the end of the GC capillary may be axially aligned, and with the interface vacuum exhaust connections, enclosed in one external port or flange of the mass spectrometer in order to increase the GC flow capacity.

Another object of the invention is to provide the means for a two-stage GC/MS molecular separator in which the outlet capillary of an external adjustable flow separator becomes the inlet capillary of an internal mass spectrometer source-attached separator so that the enrichment factor of the first stage is multiplied by that of the second stage.

Still other objects and advantages of the invention will become apparent to those of skill in the art after reading the following description of the preferred embodiments.

BRIEF DESCRIPTION OF THE DRAWINGS

FIG. 3 is cross-sectional side view of the manifold divider which may be placed in the mass spectrometer and in which view the sidearm is directed away from the viewer.

FIG. 4 is another cross-sectional side view relative to the other figures of the manifold divider in which the sidearm is directed toward the right.

FIG. 5 is another cross-sectional side view relative to the other figures of the manifold divider in which the upper and lower segments are shown.

FIG. 6 is a cross-sectional top view relative to the other figures of the manifold divider enclosing the MS source assembly.

FIG. 13 is a cross sectional view of an externally attached vacuum manifold which provided differential pumping of the first embodiment of the internal GC/MS interface.

FIG. 14 is a detailed perspective view of a micrometer drive column position mechanism which may be used with the present invention.

FIG. 15 is a cross-sectional view of an alternate separator vacuum insert for the externally attached vacuum manifold.

FIG. 16 is a cross-section of a guide support in the alternate separator vacuum insert of FIG. 14.

DESCRIPTION OF THE PREFERRED EMBODIMENTS

Figure 1:
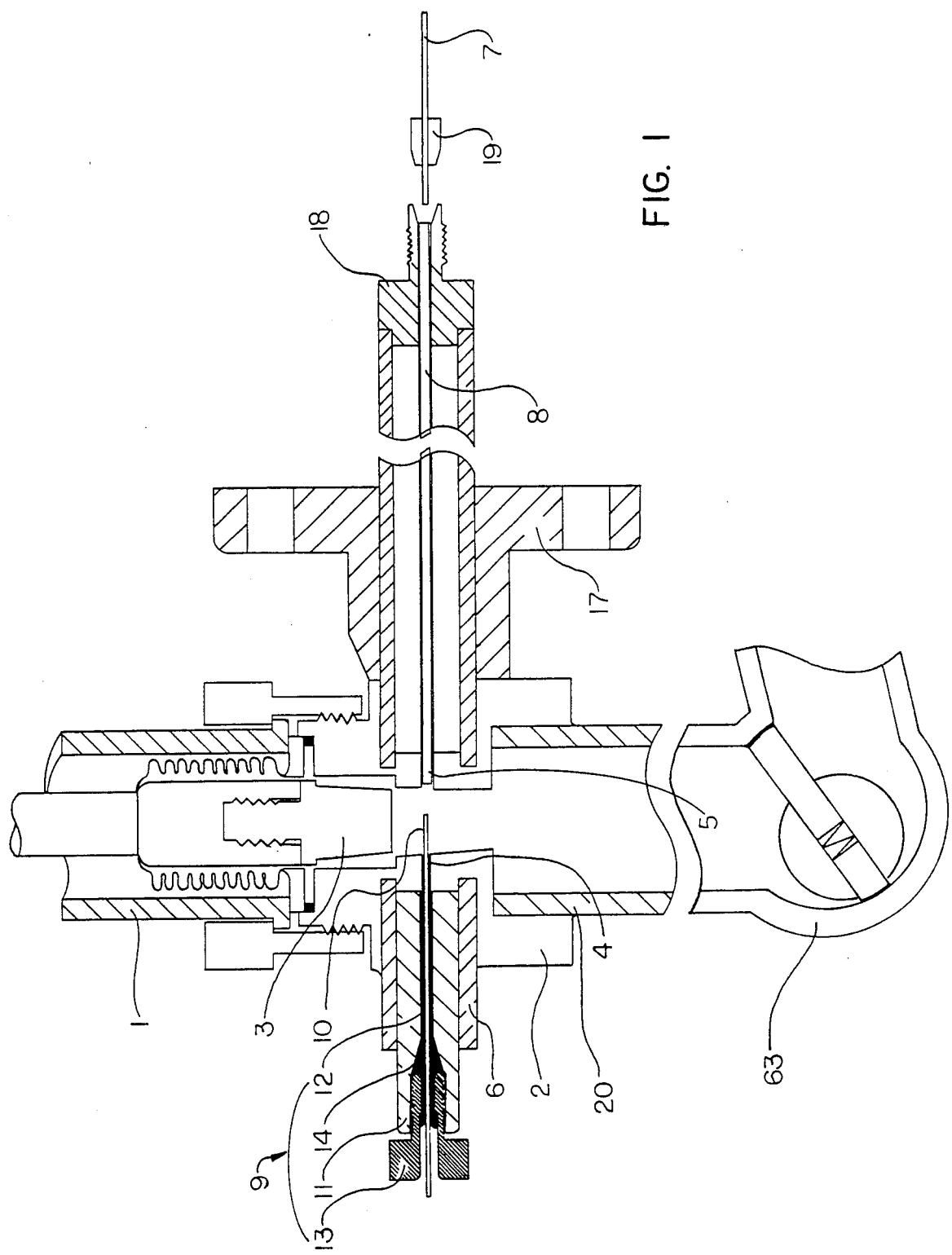
FIG. 1 is a cross-sectional view of a simplified version of the variable molecular separator or external interface of the previous invention which may be used in conjunction with the internal mass spectrometer interface of the present invention.

A cross-sectional view of a simplified version of the external interface of the previous invention (variable molecular separator) is shown in FIG. 1. The interface also serves as an isolation valve to comletely separate the gas chromatograph from the mass spectrometer so that they may be operated independently of each other. The external interface is built around a modified commercially available bellows valve with a standard bellows drive mechanism 1 in which the standard valve body is replaced by a valve body 2 which is a section of one-inch bar stock into which the 3° tapered valve seat for the valve stem 3, the GC and MS capillary guide channels 4 and 5, and sockets for the ⅜" side tubes 6 are machined. The guide channels for the fused silica capillaries may be the drilled channels themselves or in this case, the guide channel 5 for the MS transfer capillary 7 is the stainless steel needle capillary 8 inserted through the channel 5 up to the valve seat. The 1/32" zero-dead volume (ZDV) fitting 9 serves to secure the GC capillary 10. The ZDV fitting 9 consists of a slightly elongated fitting body 11 which fits inside the opening of one side tube 6 and a Vespel adapter 12 drilled to fit individual GC capillaries and which is slightly longer than standard length in order to provide increased flow impedance when the nut 13 and ferrule 14 are loosened in order to shift the position of the GC capillary 10. The adapter 12 is fabricated from a special Vespel composite (SP-3) designed to provide lubrication in order to prevent the adapter from sticking to the GC capillary 10 after exposure to high temperatures.

A vacuum flange 17 serves to fit the interface of the MS inlet flange (not shown in FIG. 1). A standard 1/16" swagelock union 18 with a Vespel ferrule 19 serves to secure the MS transfer capillary 7. A stainless steel needle capillary 8 of appropriate I.D. serves as an extended guide channel for the MS transfer capillary 7. A ⅜" I.D. stainless steel tube 20 welded in the valve body serves to connect the auxiliary or separator vacuum pump 63 to the interface. Any of several types of devices such as a micrometer drive column position mechanism may be connected on the gas chromatograph side of the interface at the ZDV fitting 9 to facilitate the changing or exact adjustment of the position of the end of the GC capillary 10 within the MS transfer capillary 7.

If the external interface of the previous invention is to be used as a vacuum lock device for sample introduction and not as a flow splitter or molecular separator, the ⅜" tube 20 may be reduced considerably in diameter to provide a connection for a smaller flexible auxiliary vacuum tube. Also, the I.D. of the capillary guide channel 5 may be made as small as practicable so that a negligible amount of air is allowed to enter the MS high vacuum when the GC capillary 10 is moved through the loosened ZDV fitting 9. In some applications, the auxiliary vacuum outlet could be eliminated entirely and access to a vacuum system could be accomplished with minimum disturbance by careful manipulation of the position of the isolation valve stem 3 and ZDV fitting 9.

Figure 2:
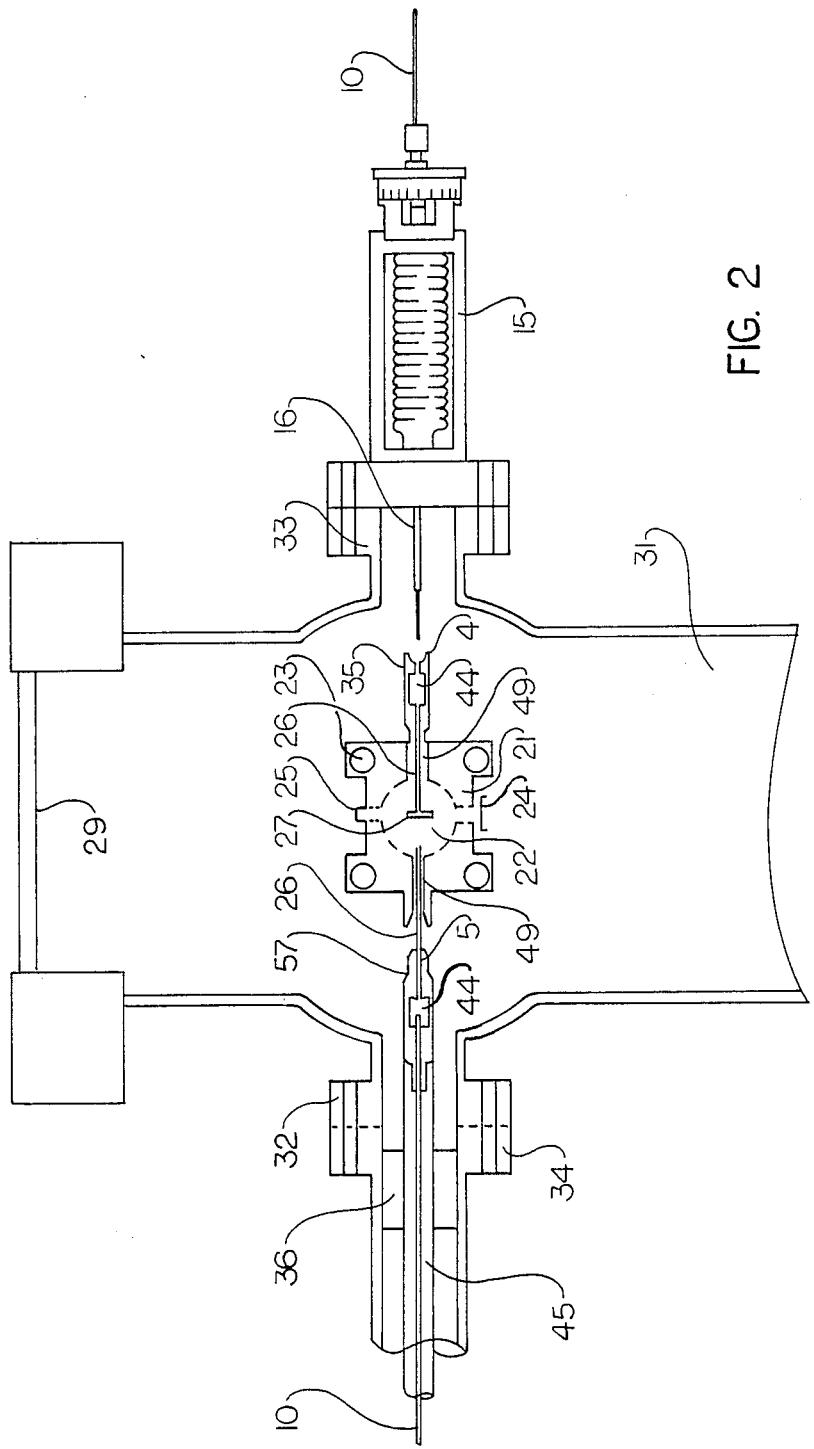
FIG. 2 is a cross-sectional view of a mass spectrometer which discloses the positions in which two embodiments of the internal GC/MS interface of this invention may be placed.

FIG. 2 shows a schematic view of a typical mass spectrometer to which each of the preferred embodiments may be attached in this invention. The first preferred embodiment, the source attached internal interface 35, and the second preferred embodiment, the probe attached internal interface 57, are both shown in this figure. The MS source body 21 surrounds the MS source cavity 22 which has a radius of approximately 2 cm and a depth of approximately 0.5 cm, and is supported by four source support rods 23. A narrow electron beam produced between the electron filament 24 and the electron collector 25 crosses the MS source cavity 22 at right angles to the axis of each of the MS transfer capillaries 26 of the two embodiments of the invention. An ion beam slit 27 in the top of the MS source body 21 allows ions produced by the impact of the electron beam on sample molecules eluting from either MS transfer Capillary 26 to emerge at right angles from the plane of the capillaries and the electron beam into the mass analyzer (not shown). For electron impact MS analysis, the MS transfer capillaries 26 will be positioned as close as possible to the electron beam without interfering with it in order to increase the probability of sample molecules becoming ionized and fragmented, without first striking the hot active surface of the MS source cavity 22.

A transparent port 29 allows visual inspection of the MS source assembly 30 (FIGS. 3, 4 and 6) and MS vacuum manifold 31. High vacuum conditions are produced in the MS vacuum manifold 31 enclosing the MS source body 21 by the MS pumping system which also causes reduced pressure in the MS source cavity 22 during a GC/MS analysis. MS inlet ports 32 and 33 allow access to MS source apertures 49 on either side of the MS source body 21. MS inlet port 33 is normally used for the GC/MS connection. FIG. 2 shows the use of a micrometer drive mechanism 15 to control the insertion of a GC capillary 10 supported by a stainless steel needle capillary guide 16, through MS inlet port 33. The needle capillary guide 16 may also be extended to engage the capillary guide channel 4 directly.

MS inlet port 32 is normally used for connecting a standard vacuum lock 34 which provides the means of inserting a direct inlet probe. The second embodiment of the invention is essentially a specially modified standard direct inlet probe 45 inserted into the mass spectrometer through MS inlet port 32 by the procedure generally used for direct inlet probes. A teflon gasket 36 enables a tight fit and proper centering of the direct inlet probe 45.

As an option to increase the efficiency of an internal interface, and as shown in FIGS. 3–6 the high vacuum manifold may be conveniently divided into a separate inner manifold 37 and the remaining annular section of the MS vacuum manifold 31 by a thin cylindrical shell 38. This easily removable cylindrical shell 38 may produce separate source and interface vacuum exhaust columns whose conductance ratio is determined by their cross-sectional dimensions, provided that the cross-conductance between the vertical columns is reduced to negligible levels. Careful consideration must be taken of the conductance ratio required depending on the carrier gas split and sample enrichment in the interface. The shell is composed of upper and lower sections joined in the middle by a thin vespel ring 39 (FIG. 3) which has two continuous vertical slots (not shown) into which the upper and lower sections fit. A manifold divider sidearm 40 to the cylinder encloses the electrical and mechanical feedthroughs required for source control. With the addition of an auxiliary high vacuum exhaust port in the outer wall, true differential pumping of the source and separator effluents can also be accomplished. The MS analyzer tube 41 (FIGS. 4 and 6), which has a small entrance slit, is differentially pumped by a separate mass analyser high vacuum pumping system (not shown). Differential pumping of the interface will permit much higher GC flow rates to be used since much higher pressures can be tolerated in the outer manifold. Loss of sensitivity can be kept at a minimum level, provided that reasonable sample enrichment levels can be achieved in this internal interface.

Figure 9:
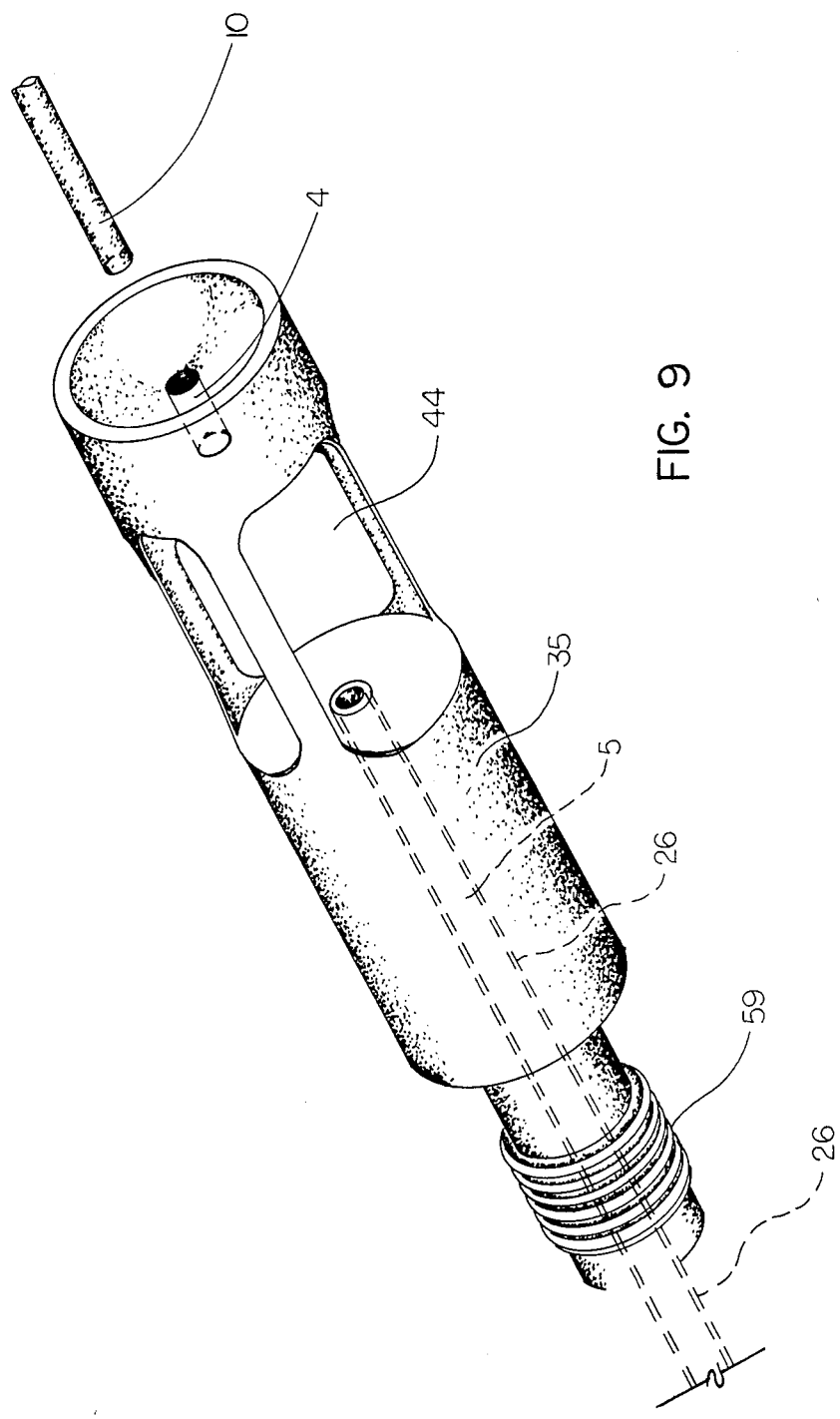
FIG. 9 is a perspective view of a one-piece version of the first embodiment of the internal GC/MS interface.
Figure 11:
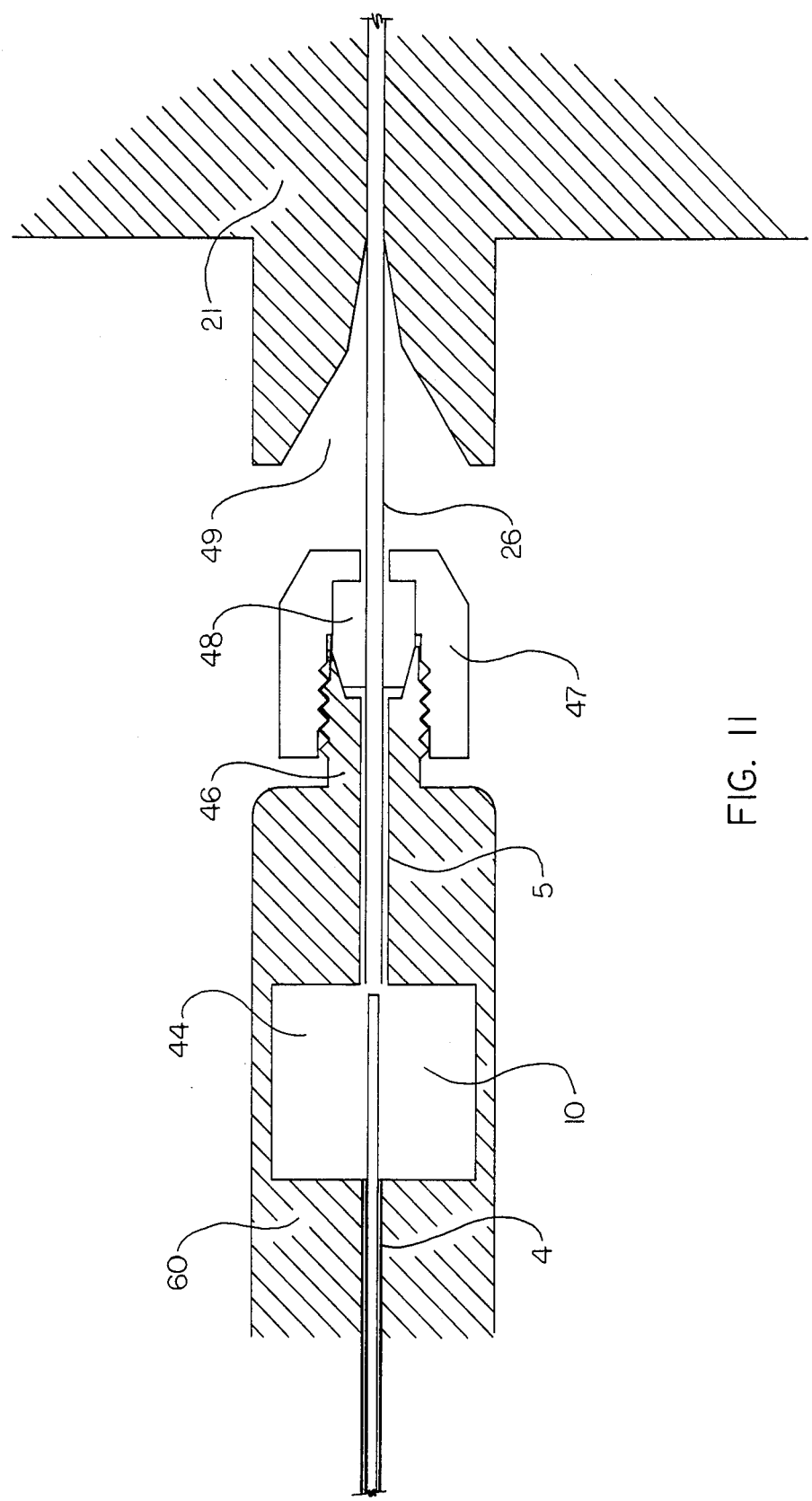
FIG. 11 is a cross sectional view of a second embodiment of the internal GC/MS interface which is attached to a direct inlet probe.

Although both embodiments of the invention may serve any or all of the stated objectives of the invention, it will in general be more convenient to use one or the other for a given application with a particular mass spectrometer instrument because of limited access to one of the MS ports. Both embodiments of the invention may be constructed so that the fused silica transfer capillary may be easily exchanged or discarded. There are, however, definite advantages such as low cost, simple construction, and increased alignment accuracy for a one-piece construction where the MS transfer capillary is permanently attached to a one-piece interface as shown in FIGS. 9 and 11 (See below). In addition, in both embodiments the MS transfer capillary 26 may be tapered to be narrower at the MS source end in order to increase the flow impedance in the interface and thus to increase the pressure in the MS transfer capillary.

Figure 7:
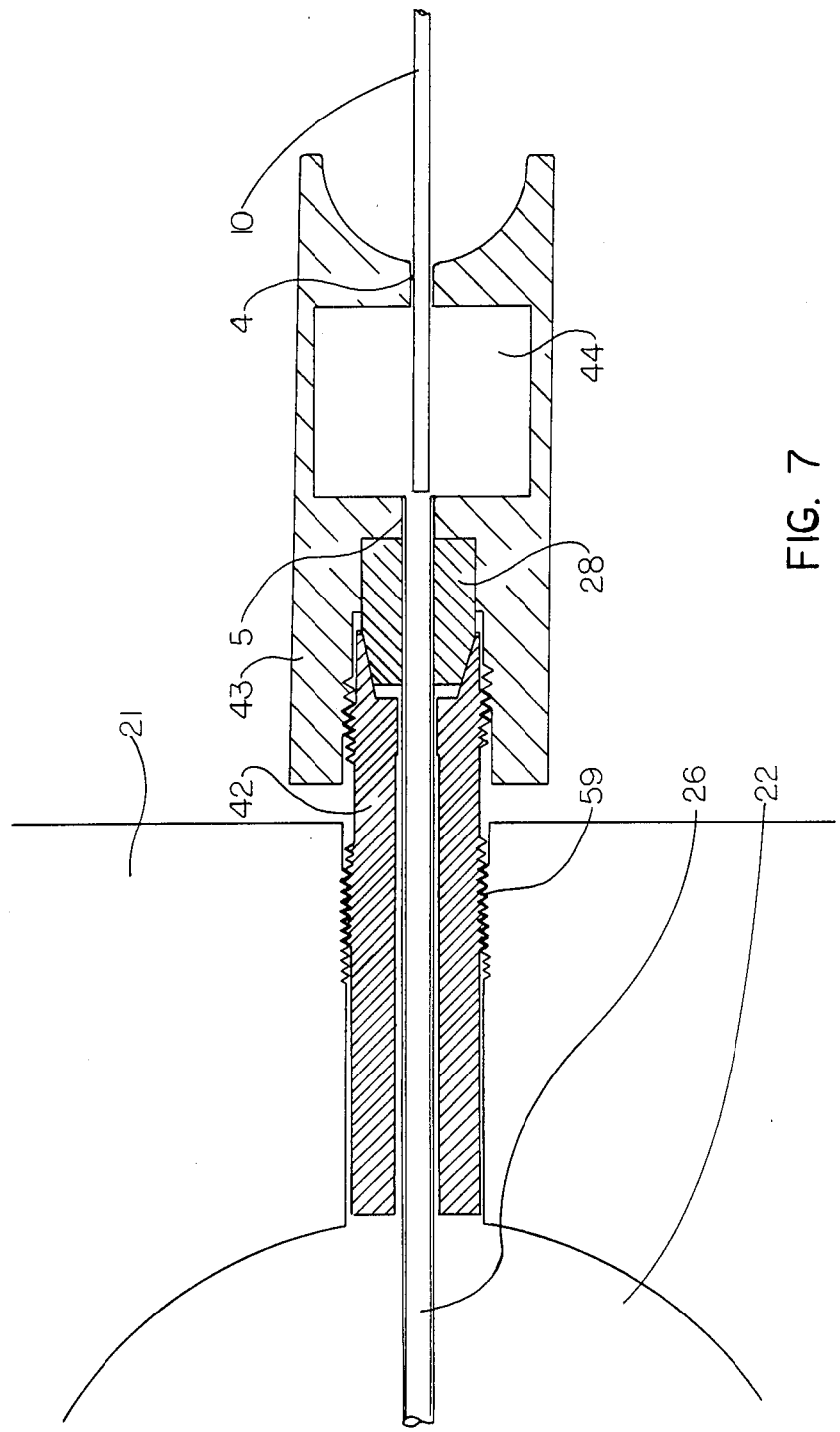
FIG. 7 is a cross-sectional elevational view of a first embodiment of the internal GC/MS interface which may be directly attached to the MS source.
Figure 8:
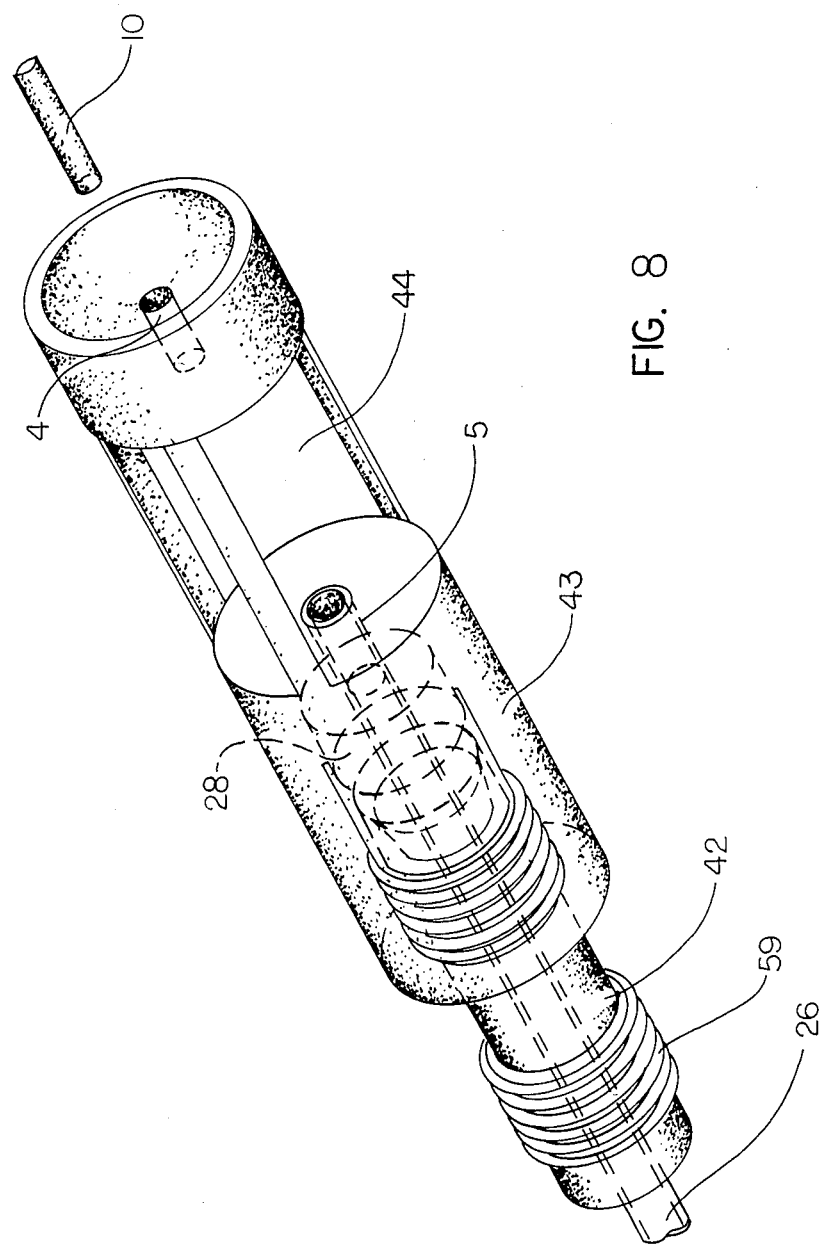
FIG. 8 is a perspective view of the first form of the internal GC/MS interface which may be directly attached to the MS source.

In the first embodiment of the invention, shown in detail in FIGS. 7 and 8, the source interface attachment is essentially composed of a modified 1/16" swage lock union 42 for which a specially machined 1/16" nut 43 has been constructed. A machined hole in this nut 43 will provide the interface gap 44 and serve to align the GC capillary 10 and the MS transfer capillary 26 across the gap by means of the opposing capillary guide channels 4 and 5. These channels are drilled so that the GC capillary 10 and the MS transfer capillary 26 fit exactly within them. The entrance to the GC guide channel 4 has an enlarged aperture with beveled sides so that any inserted GC capillary or any other capillary is guided into the channel and becomes exactly aligned with the MS transfer capillary 26 across the interface gap 44 and can pass into it without obstruction.

The relative dimensions of the first embodiment of the interface may vary considerably depending on the requirements of different instrument designs and of different applications. The minimum length of the two capillary guide channels 4 and 5 is generally determined by the alignment tolerance required for different sets of interface capillaries to be used. The main body of the swagelock union 42 and a vespel ferrule 28 have also been drilled out to fit the outer dimensions of the MS transfer capillary 26.

Finely spaced threads 59 on the pipe end connection of the swagelock union 42 to the MS source body 21 (FIG. 7) insure a very low conductance across the connection and provides an accurate and stable adjustment of the end of the MS transfer capillary 26 with respect to the electron beam at the center of the MS source cavity 22.

It may be convenient and useful to fabricate this entire interface from a single piece of stainless steel bar stock as shown in FIG. 9 and to permanently attach the MS transfer capillary 26 to the one-piece interface 35. The functions and relative locations of the GC capillary 10, the guide channels 4 and 5, the interface gap 44, and the MS transfer capillary 26 would be the same as in the multiple piece interface shown in FIGS. 7 and 8.

Figure 10:
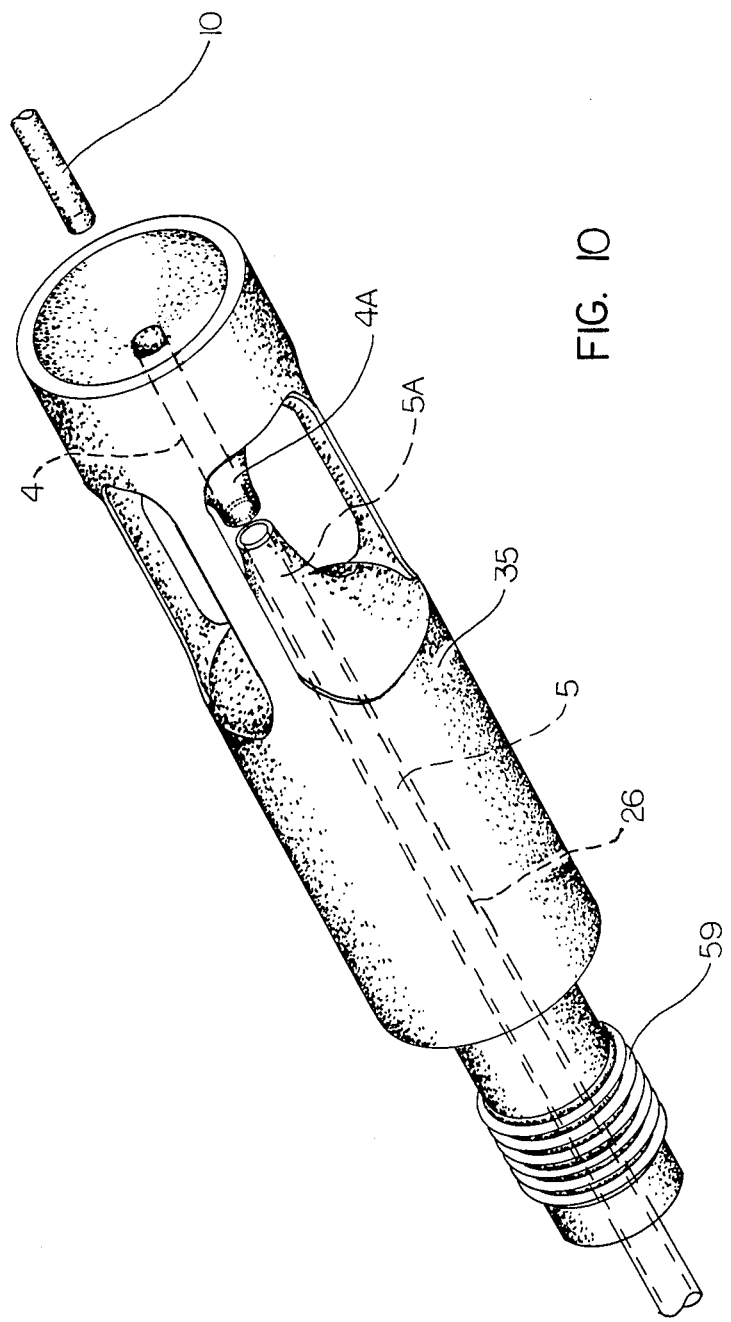
FIG. 10 is a perspective view of a one-piece verson of the first embodiment of the internal GC/MS interface in which the gap distance is reduced.

When the interface gap 44 in the first embodiment (or in the second embodiment) is at least 6 mm wide, both the carrier gas transmission and the enrichment factor approach a minimum as the GC capillary 10 is withdrawn across the interface gap 44. The minimum value is useful as reference point in performance evaluation of the interface. A narrow gap insures good alignment but reduces gap conductance. In order to make the gap conductance as large as possible the cutaway space is as large as possible and only enough support material is left to maintain the mechanical rigidity and alignment of the interface. It may be possible to reduce the gap to as low as one mm or less in practical applications. For a very narrow gap, the cut-away contour of the interface gap 44 must be designed so that the gap conductance does not become the limiting factor in determining gap pressure when the GC capillary 10 is withdrawn from the MS transfer capillary 26. This is shown in FIG. 10, where the gap distance is reduced considerably compared to the interface of FIG. 8, with only a slight reduction in the flow conductance of the gap, by the construction of extended guide channels 4a and 5a.

Figure 12:
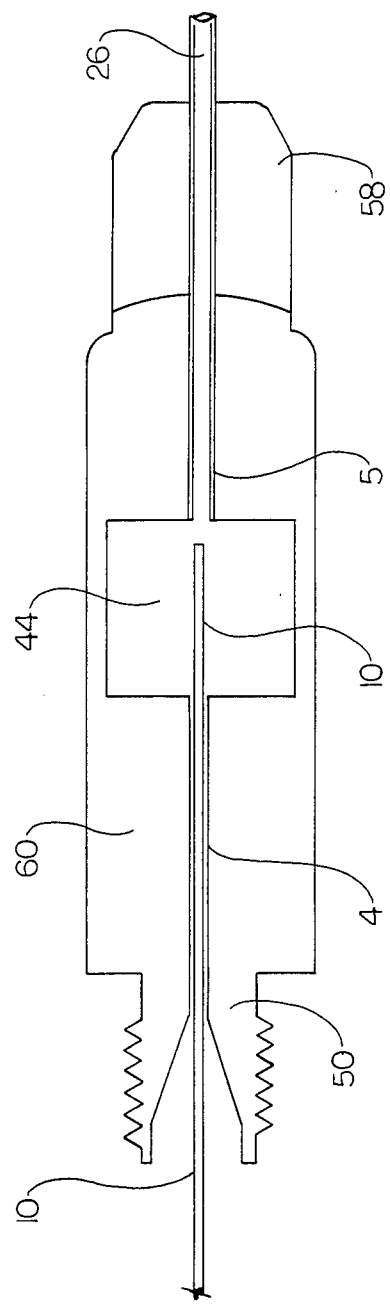
FIG. 12 is a cross sectional view of an alternate one-piece construction version of the second embodiment of the internal GC/MS interface.

In the second preferred embodiment shown in FIGS. 11 and 12, an interface is machined directly from a material such as $\frac{3}{8}''$ stainless steel rod which may be introduced into the mass spectrometer through a standard vacuum lock in exactly the same manner as a conventional direct inlet probe (FIG. 2). In this embodiment of the invention, guide channels 4 and 5 for the GC capillary 10 and the MS transfer capillary 26 respectively, are drilled into the interface direct inlet rod 60 at opposite ends of the interface gap 44. A standard 1/16" swagelock fitting 46 machined into the end of the rod along with a 1/16" nut 47 and Vespel ferrule 48 serves to secure the MS transfer capillary 26. The nut 47 which is fabricated from Vespel (SP-1) to prevent electrical grounding of the MS source, has a beveled head which mates with the inlet orifice 49 of the inlet channel in the source to provide a seal. Only a slight modification is required of the inlet orifice 49 so that it will accept and align first the tip of the short MS transfer capillary 26 and then the Vespel nut 47 at the end of interface as the probe is inserted through the direct inlet vacuum lock 34 (FIG. 2) and forced tightly against the MS source body 21. This configuration will allow an off angle approach of both the interface and the short but flexible MS transfer capillary 26 to result in proper alignment of the MS transfer capillary 26. Since the interface direct inlet rod 60 is held in position by a relatively soft teflon gasket 36 (FIG. 2) at about 10 cm distance, some misalignment of its tip is expected.

Because it is difficult to drill small diameter channels in stainless steel for long distances it is more convenient in preparing the interface direct inlet rod 60 to use a stainless steel needle capillary of appropriate inner diameter as the guide tube through the long (about 30 cm) 3/16" ID interface direct inlet rod 60 providing a snug fit with the guide channel 4 only at the end. Alternatively, the main channel in the interface direct inlet rod 60 could be quite large with a small tapered channel at the MS end of the probe interface to guide the GC capillary 10 into the guide channel 4. A narrow annular channel around the GC capillary 10 restricts the air flow to the MS when a ferrule in the inlet end of the rod (not shown) is loosened in order to adjust the position of the GC capillary 10.

As with the first embodiment, it will also be useful in some circumstances to construct this embodiment as a one-piece interface as shown in FIG. 12 in which the swagelock fitting 46, the nut 47 and Vespel ferrule 48 of FIG. 11 are omitted. An insulating material 58 such as Vespel is used to coat the beveled end of the direct inlet rod 60. Again, the relative positions and functions of the GC capillary 10, the interface gap 44, the guide channels 4 and 5, and the MS transfer capillary 26 would remain the same as in the multiple piece interface shown in FIG. 11. The interface is a one-piece construction having a pipe fitting connector end 50 which may be screwed into the direct inlet rod 45 (FIG. 2).

As shown in FIG. 13, with the first embodiment, the invention may also be used with an externally attached vacuum manifold. A standard "T" 51 preferably with an inside diameter of $\frac{5}{8}''$ or greater is connected between the MS manifold port 33 (shown in FIG. 2 as well) and a device to control the position of the GC capillary 10 in relation to the MS transfer capillary 26. In this case, a micrometer drive mechanism 15 is used which is shown in more detail in FIG. 14. The micrometer drive mechanism 15 may have a range of 1.5 cm with ±0.05 mm resolution. The ZDV fitting 52 which secures the GC capillary 10 (FIG. 14) is the same type as the ZDV fitting 9 in FIG. 1. The stainless steel needle capillary guide 16 shown extending from the mechanism in FIGS. 2 and 13 has a free end extending through the micrometer drive mechanism 15 up to the ZDV fitting 52.

The other outlet of the standard "T" 51 is connected to a high vacuum pump 63 or high speed rotary pump (not shown) by means of a vacuum outlet 53. An inner cylinder, the separator vacuum insert 54, provides the means of separating the exhaust systems by enclosing the internal source attached interface 35 and sliding snugly through the MS port 33.

As shown in FIG. 15, the end of the separator vacuum insert 54 which is within the "T" 51 may have threads 61 to allow the separator vacuum insert 54 to be held more firmly against the MS source body 21. A Vespel end piece 55 may be placed on the MS end of the separator vacuum insert 54 to insure low cross conductance of the two vacuum systems. The degree of cross conductance which occurs will depend on the overall pumping capacities and the pressure gradient between the two systems. In any case, cross conductance can be reduced to negligible levels by straight-forward design modifications at the contact point to provide a tightened seal. An inner ring, shown in cross section in FIG. 16, on the needle guide capillary support 56 or any number of similar devices can be used to roughly center the flexible needle guide capillary 16 extending from the position control mechanism 15. Alternatively, the needle guide capillary 16 may be extended to fit into the capillary guide channel 4.

I claim:

1. A gas chromatograph/mass spectrometer interface system for connecting a gas chromatograph output means to a mass spectrometer source, which comprises:
   (a) an output column having a first end and a second end;
   (b) an elongated rigid interface body having a first interface end and a second interface end, and having an interface gap positioned between the first interface end and the second interface end, said first interface end having a first bore extending therethrough to the interface gap for insertion of the gas chromatograph output means, said second interface end having a second bore extending therethrough to the interface gap for insertion of the output column, the output column being positioned such that its second end is located within the second bore, and said first bore and said second bore being axially aligned across the interface gap;
   (c) a means for moving the gas chromatograph output means through the first bore, across the interface gap and into the second bore;
   (d) a means for securing the interface to a mass spectrometer such that the first end of the output column is positioned in the mass spectrometer source; and
   (e) a vacuum means connected to the mass spectrometer source.

2. A gas chromatograph/mass spectrometer interface system for connecting a gas chromatograph output means to a mass spectrometer source as recited in claim 1, wherein the vacuum means connected to the mass spectrometer source comprises a mass spectrometer vacuum system.

3. A gas chromatograph/mass spectrometer interface system for connecting a gas chromatograph output means to a mass spectrometer source as recited in claim 2, in which the interface gap is from 0.1 to 6 mm wide.

4. A gas chromatograph/mass spectrometer interface system for connecting a gas chromatograph output means to a mass spectrometer source as recited in claim 2, further comprising a vacuum pump external to the mass spectrometer vacuum system for separate evacuation of the interface, said vacuum pump being connected to the interface by a tube means surrounding the interface gap.

5. A gas chromatograph/mass spectrometer interface system for connecting a gas chromatograph output means to a mass spectrometer source as recited in claim 2, wherein the vacuum means connected to the mass spectrometer source further comprises a separate vacuum pump being connected to an outer manifold within the mass spectrometer vacuum system and providing separate evacuation of the mass spectrometer source and the interface body.

6. A gas chromatograph/mass spectrometer interface system for connecting a gas chromatograph output means to a mass spectrometer source as recited in claim 2, wherein the inner diameter of the first end of the output column is smaller than the inner diameter of the second end of the output column.

7. a gas chromatograph/mass spectrometer interface system for connecting a gas chromatograph output means to a mass spectrometer source as recited in claim 2, in which the first bore is widened and beveled at the first interface end.

8. A gas chromatograph/mass spectrometer interface system for connecting a gas chromatograph output means to a mass spectrometer source as recited in claim 2, wherein the interface body is formed in one piece.

9. A gas chromatograph/mass spectrometer interface system for connecting a gas chromatograph output means to a mass spectrometer source as recited in claim 2, wherein the portion of the first interface end adjacent to the interface gap and surrounding the first bore conically protrudes into said interface gap and wherein the portion of the second interface end adjacent to the interface gap and surrounding the second bore conically protrudes into said interface gap.

10. A gas chromatograph/mass spectrometer interface system for connecting a gas chromatograph output means to a mass spectrometer source as recited in claim 2, wherein a stainless steel guide needle capillary is securely fitted into the first bore, said stainless steel guide needle capillary having an inside diameter wide enough to accomodate the gas chromatograph output means.

11. A gas chromatograph/mass spectrometer interface system for connecting a gas chromatograph output means to a mass spectrometer source as recited in claim 2, wherein the means for securing the interface to a mass spectrometer comprises external threads on the second interface end.

12. A gas chromatograph/mass spectrometer interface system for connecting a gas chromatograph output means to a mass spectrometer source as recited in claim 11, wherein the interface body is formed in one piece.

13. A gas chromatograph/mass spectrometer interface system for connecting a gas chromatograph output means to a mass spectrometer source as recited in claim 12, wherein the second end of the output column is fixed within the second bore of said interface body.

14. A gas chromatograph/mass spectrometer interface system for connecting a gas chromatograph output means to a mass spectrometer source as recited in claim 2, wherein the interface body is comprised of stainless steel and includes a beveled fitting at the second interface end furthest from the interface gap, said beveled fitting being comprised of an insulating material and being capable of being sealingly fitted to a mass spectrometer source body having a beveled bore.

15. A gas chromatograph/mass spectrometer interface system for connecting a gas chromatograph output means to a mass spectrometer as recited in claim 14, wherein the vacuum means connected to the mass spectrometer further comprises a separate vacuum pump being connected to an outer manifold within the mass spectrometer vacuum system and providing separate evacuation of the mass spectrometer source and the interface body.

16. A gas chromatograph/mass spectrometer interface system for connecting a gas chromatograph output means to a mass spectrometer as recited in claim 14, wherein the inner diameter of the first end of the output column is smaller than the inner diameter of the second end of the output column.

17. A gas chromatograph/mass spectrometer interface system for connecting a gas chromatograph output means to a mass spectrometer source as recited in claim 14, wherein a stainless steel guide needle capillary is securely fitted into the first bore, said stainless steel guide needle capillary having an inside diameter wide enough to accommodate the gas chromatograph output means.

18. A gas chromatograph/mass spectrometer interface system for connecting a gas chromatograph output means to a mass spectrometer source as recited in claim 2, wherein the interface body is formed in one piece having a beveled end, said beveled end being coated with an insulating medium and being sealingly fitted to a mass spectrometer source body having a beveled bore.

19. A gas chromatograph/mass spectrometer interface system for connecting a gas chromatograph output means to a mass spectrometer source as recited in claim 18, wherein the second end of the output column is fixed within the second bore of said interface body.

20. A gas chromatograph/mass spectrometer interface system for connecting a gas chromatograph output means to a mass spectrometer source as recited in claim 19, wherein the inner diameter of the first end of the output column is smaller than the inner diameter of the second end of the output column.

* * * * *